United States Patent
Dang et al.

(10) Patent No.: US 11,674,107 B2
(45) Date of Patent: Jun. 13, 2023

(54) PROCESS FOR PRODUCING MICROEMULSION SYSTEM OF NANO ESSENTIAL OIL

(71) Applicant: Wakamono joint stock company, Ho Chi Minh (VN)

(72) Inventors: Hong Ngoc Thi Dang, Ho Chi Minh (VN); Nam Hai Lai, Ho Chi Minh (VN)

( * ) Notice: Subject to any disclaimer, the term of this patent is extended or adjusted under 35 U.S.C. 154(b) by 215 days.

(21) Appl. No.: 16/835,940

(22) Filed: Mar. 31, 2020

(65) Prior Publication Data

US 2021/0277325 A1    Sep. 9, 2021

(51) Int. Cl.
*C11B 9/00* (2006.01)
*A61K 8/06* (2006.01)
*A61K 9/107* (2006.01)

(52) U.S. Cl.
CPC .............. *C11B 9/00* (2013.01); *A61K 8/068* (2013.01); *A61K 9/1075* (2013.01)

(58) Field of Classification Search
CPC ......... C11B 9/00; A61K 8/068; A61K 9/1075; A61K 2800/10; A61K 8/375; A61K 8/553; A61K 8/922; A61Q 19/00
See application file for complete search history.

*Primary Examiner* — David J Blanchard
*Assistant Examiner* — Thurman Wheeler
(74) *Attorney, Agent, or Firm* — Fulwider Patton LLP

(57) ABSTRACT

The invention relates to the process for producing an microemulsion system of nano essential oil, the process comprising the following steps: (i) preparing a dispersed phase of essential oil; (ii) preparing of a carrier formed from a mixture of diethylene glycol monoethyl ether and lecithin; (iii) adding the carrier to the dispersed phase while keeping the dispersed phase temperature between 60 and 100° C. after addition of the carrier, while simultaneously stirring under vacuum; then pass the entire solution mixture through the system of high-pressure homogeneous machine integrated dispersion nozzle; (iv) adding the solution mixture obtained in step (iii) to Capryol 90 while keeping the mixture temperature between 60 and 100° C., and stirring at a rate ranging from 400 up to 800 rpm under vacuum; (v) cooling the mixture, homogenizing the mixture by ultrasonication to achieve a droplet size smaller than 100 nm.

4 Claims, 1 Drawing Sheet

PROCESS FOR PRODUCING MICROEMULSION SYSTEM OF NANO ESSENTIAL OIL

CROSS-REFERENCES TO RELATED APPLICATIONS

This application claims priority from Vietnam Application No. 1-2020-01333, filed Mar. 6, 2020, incorporated by reference in its entirety.

FIELD OF THE INVENTION

The invention relates to a process for producing a microemulsion system of nano essential oil.

BACKGROUND OF THE INVENTION

Concentrated essential oil liquid forms of substances are in nature volatile, which are present in aromatic plants. Essential oils are used in medicine as main active ingredients or as drug delivery compounds, in addition to being used extensively in cosmetics, food, and industry.

Essential oils have been extracted from several major plant families, such as the Abietaceae Pine (best known as *Pinus merkusii* pine essential oil, which is a source of pine essential oil, resin and rosin), the Cupressaceae (*Biota orientalis, Platycladus orientalis, Araucaria excelsa* (*Araucaria heterophylla*)), the Lamiaceae (basil, lavender, marjoram, perilla, peppermint, patchouli, rosemary), the Sim Myrtaceae (eucalyptus, clove, Rose myrtle, Melaleuca), Lauraceae (cinnamon, laurel, rosewood, nutmeg, *Sassafras albidum*), Rutaceae (lemon, lime, mandarin, orange, grapefruit), Asteraceae (chrysanthemum, tarragon, sweet inula, gray santolina), Poaceae and Rosaceae, etc. Essential oils have been used to treat inflammatory diseases, pain, gastrointestinal diseases, stress, etc. Modern pharmacological studies have shown that essential oils have many remarkable biological activities: antifungal, antibacterial, and anti-inflammatory activities, pain relief, protection of nervous system, anti-insect activities, etc. Essential oils are also widely used in aromatherapy. This is a natural therapy using essential oils extracted from plants to treat diseases. This therapy has been shown to take effects in mood enhancement, pain relief, cognitive function improvement, and is getting more commonly used in complementary or alternative medical (CAM) therapies or in primary health care. Numerous studies have demonstrated the sedative effect of rose, lavender, lemon and peppermint essential oils (Lehrner et al. 2005, B. F. Bradley et al., 2007). Some recent studies have investigated the essential oil ingredients with sedative effect and molecular mechanisms thereof: linalool is the main ingredient with sedative effect in lavender essential oil (T. Umezu et al., 2006); lemon essential oil has the effect of increasing the neural energy of 5-hydroxy tryptamine through inhibition of dopamine activity (M. Komiya et al., 2006); peppermint essential oil can stimulate dopamine—an ingredient involved in mouse movement. Wu et al. (2012) performed a comprehensive study on metabolism in mouse brain tissue and urinary reactions in aromatherapy. Metabolic changes include an increase in sugar compounds and a decrease in neurotransmitters (tryptophan, serine, glycine, aspartate, histamine, tyrosine, cysteine, phenylalanine, hypotaurine, histidine, asparagine), amino acids and fatty acids in the brain. High levels of aspartate and sugar compounds (sucrose, maltose, fructose and glucose), nucleosides (adenine, uridine) as well as organic acids like lactate and pyruvate have been found in urine. All these studies have shown that odors can produce specific effects on human autonomic and neuropathological functions, showing that aromatherapy has beneficial effect in the modern context of increasing stressful and unhealthy mental factors.

With the properties of aromatic substances and antifungal, antibacterial, and antioxidant effects, essential oils are used in many cosmetics such as soap, toothpaste, cleaning products, perfumes, fragrances, etc. In addition, many essential oils also have good UV protection and antioxidation so they are used in skin protective cosmetics for anti-aging and prevention of damaging effects by UV. Some typical examples are: sesame oil prevents 30% of UV rays; coconut oil, peanut oil, olive oil, cottonseed oil have 20% UV protection effects (Korać R R et al., 2011). Antibacterial and anti-inflammatory effects of essential oils have also been applied to toothpaste products, mouthwash, etc. to simulataneously form good breath and treat durationontal diseases, and gingivitis.

Essential oils are antioxidant, antibacterial, antifungal so they have been applied to food preservation. Several studies have shown that essential oils have a broad antimicrobial effect against *Listeria monocytogenes, Salmonella typhimurium, Escherichia coli* O157: H7, *Shigella dysenteria, Bacillus cereus* and *Staphylococcus aureus* with MIC values of 0.2 to 10 µM. Some components in the essential oils have been determined with good antibacterial activity such as carvacrol, thymol, eugenol, perillaldehyde, cinnamaldehyde, and cinnamic acid with minimum inhibitory concentration (MIC) of 0.05 to 5 µM in vitro. In higher concentrations, the antimicrobial effect is similar to that used in food: research with fresh meat, meat products, fish products, milk, dairy products, products derived from vegetables, fruits and rice has shown that the required concentration of essential oils to achieve good antimicrobial effects is about 0.5-20 µg/g of food and about 0.1-10 µl/l in fruit and vegetable washing preparations. The antimicrobial effect of the essential oils can be explained since essential oils include a large number of components and their activities are related to a number of targets in bacterial cells. The hydrophobicity of essential oils allows them to penetrate and separate the lipids of bacterial cell membranes and mitochondria, causing seepage and leakage of cell organelles. The physical conditions to enhance the effect of the essential oils include low pH, low temperature, and low oxygen concentration.

The below table represents some currently common essential oils:

| No. | Name of essential oil | STT | Name of essential oil | No. | Name of essential oil |
|---|---|---|---|---|---|
| 1 | Basil | 12 | Rose | 24 | Amber |
| 2 | Bergamot | 13 | Rosemary | 25 | Black tea |
| 3 | Black pepper | 14 | Tea tree | 26 | Tabac |
| 4 | Cedarwood | 15 | Thyme | 27 | Fig leaf |
| 5 | Clove | 16 | Ylang Ylang | 28 | Ambroxan |
| 6 | Frankincense | 17 | Grapefruit | 29 | Daisy |
| 7 | Geranium | 18 | Vetiver | 30 | Saffron |
| 8 | Lavender | 19 | Sandalwood | 31 | Oud |
| 9 | Nutmeg | 20 | Musk | 32 | Whisky wine |
| 10 | Palmarosa | 21 | Jasmine | 33 | Rum |
| 11 | Patchouli | 22 | Magnolia flower | 34 | Cinnamon |

However, the natural essential oil has a disadvantage of being volatile if it is not well preserved and can be denatured by light, and temperature. Direct use of the essential oils causes irritation in the skin and eyes, especially in people with sensitive skin and children. Although the demand for the use of essential oils in cosmetics, food, pharmaceuticals and even agriculture is huge, due to being instable, easily denatured, insoluble, lighter than water, and more easily vesiculated, the essential oils are limited in their applications.

Therefore, it is necessary to improve stability, reduce denaturation during production, improve water dispersibility, and increase bioavailability of various oils. Further, the application of nanotechnology as a new technological application to form a drug delivery system and increase the bioavailability of the substances in general is attracting a lot of research interest, one of which is the process for producing microemulsion system of nano essential oil.

WO2014/065346 (V. Mane Fils), published on May 1, 2014, relates to a process for preparing an oil-in-water microemulsified product of terpene-containing essential oil, such as peppermint, grapefruit essential oils, the process comprises: (i) preparing a dispersed phase by mixing a terpene containing oil with ethanol to form a dispersed phase, (ii) mixing Poem J-0021 and Polysorbat 80 into an emulsifier in association with heating to provide an O/W emulsion system consisting of (A) a terpene-containing essential oil, (B) ethanol, (C) a polyglycerol fatty acid ester, and (D) a sorbitane polyoxyethylene fatty acid ester, and wherein (A):(B)=1:2.5-40 by weight. Since the maximum ratio of the terpene-containing essential oil in the system is very low and unstable as 2.5%, this process is used to form a preparation for direct skin application, which cannot be applied to other products.

CN105640846 A (Wang Lu), published on Jun. 8, 2016, relates to a method of making a peppermint essential oil emulsion preparation for direct skin application with whitening effect, in which the method comprises mixing by weight: 26-30 parts of peppermint essential oil, 28-32 parts of tween 80, 24-28 parts of methylisothiazolinone, 22-26 parts of high fatty acid, 24-28 parts of lecithin, water and other auxiliary components, and high-speed ultrasonicating. CN105640846 A applies only to peppermint essential oil in emulsion cream system used in skin cosmetics, the main components of which such as peppermint essential oil, fatty acids, lecithin, and tween are all oil-based substances, the method comprises 26-30 parts of peppermint essential oil, however, in order to introduce the essential oil amount into the product, it is required to use up to 24-28 percent of methylisothiazolinone which is a preservative with toxic and skin irritating effects and has been banned for use in any product since May 2019 under the ASEAN Cosmetic Treaty. A process according to CN105640846 A does not form an oil-in-water microemulsion system, and an essential oil nano carrier that disperses well in water, using user-friendly and safe substances, but only forms an oil-based product for topical application with a whitening effect, which is an opaque system, and insoluble in water. This is an emulsion system that does not occlude essential oils, and the essential oils are not stable in a long term and cannot be applied to other products.

CN104825351 A (Dongguan Boton Flavoes & Fragrances Co. Ltd.), published on Aug. 12, 2015, relates to a process for preparing an emulsifying facial cleanser with a whitening effect from agarwood essential oil, this process comprises: (i) adding and mixing deionized water, 1-1.5% of lecithin, 2-4% of TWEEN 80, 4-8% of vitamins and 7-15% of pyrrolidone polyethylene glycol of carboxylic acid with slow stirring and the temperature raised to 90° C.; (ii) adding cocamidopropyl betaine, uniformly stirring and slowly cooling to 50° C., followed by addition of citric acid and further stirring and cooling to 40° C., then adding 2-8% of agarwood essential oil, 5-18% of herbal extract, 2-10% of aloe vera extract, and keeping stirring to get the final product. The process described in this document is to form a facial cleanser that only contains 2-8% of essential oils, in which the microemulsion system is unstable in a long term, but it is not able to form a microemulsion system of nano essential oil that is stable and dispersible in water for application to a wide range of products, and the required amount of essential oils introduced into the system needs to be up to 30%.

In general, the aforementioned processes mainly produce microdroplets with a size larger than 100 nm, so the dispersion efficiency in water is not high, and the stability time is short, not meeting requirements if applied to actual product. The studies in experimental models, the use of complex equipment and steps make it difficult to be applicable on an industrial scale and cannot be adjusted to form a desired droplet size to apply to each product type, especially with the low contents of essential oils in the system of less than 20% while using PEG, thus do not meet the demand for use.

Therefore, there is a need for a process for producing a microemulsion system that allows the formation of oil microdroplets with a droplet size of, as desired by the manufacturer, less than 100 nm, and a high oil content ratio of over 30% without using synthetic PEG in the process, which ensures safety and may suggest that the products are made from natural materials, may form uniform droplets with long-term stability of within two years, have better dispersibility in water, and are long-term stable in water systems while maintaining a stable structure. The activities of the active substances and microemulsified droplets must be stable in the industrial production process, and have high applicability in food, pharmaceuticals, and cosmetics.

SUMMARY OF THE INVENTION

It is an object of the present invention to provide a process for producing a microemulsion system of nano essential oil that allows the formation of uniformly sized droplets which are capable of dissolution and long-term stability in water with no activity or structure changes, helping to increase the use efficiency of essential oils, namely increasing the absorption and the bioavailability that are applicable on an industrial scale; in particular, a process according to the invention forms a microemulsion system of nano essential oil that ensures safety and may suggest that the products are made from natural materials, may form uniform droplets of smaller than 100 nm, the product contains high contents of essential oils of 30% with long-term stability, better dispersion in water and long-term stability in the water systems while retaining stable structures of essential oils.

To achieve the above object, the invention proposes a process for producing a microemulsion system of nano essential oil comprising the following steps:
(i) preparing a dispersed phase by heating an essential oil to a temperature between 60 and 100° C.;
(ii) preparing a carrier by heating a mixture of Transcutol P (diethylene glycol monoethyl ether) and lecithin at the weight ratio of between 5:1.5 and 6:1 to a temperature between 60 and 100° C. under vacuum by using a rotary vacuum evaporator system, followed by cooling the mixture to 30° C., then respectively ultrasonicating for 30 minutes, magnetic stirring, and heating at a temperature between 60 and 100° C. for 30 minutes, collecting the solution and introducing into the rotary vacuum evaporator system, and continuing to stir at 100° C.;

(iii) adding the carrier to the dispersed phase at the weight ratio of between 2:1.5 and 2:1 while keeping the dispersed phase temperature between 60 and 100° C. after addition of the carrier, while simultaneously stirring at a rate ranging from 400 to 800 rpm under vacuum; then passing the entire solution mixture through a high-pressure homogenizer integrated with a dispersion nozzle;

(iv) adding the solution mixture obtained in step (iii) to Capryol 90 (propylene glycol monocaprylate) at the weight ratio of between 4:1.5 and 4.5:1 while keeping the mixture temperature between 60 and 100° C. after the addition of Capryol 90, then stirring at a rate ranging from 400 to 800 rpm under vacuum;

(v) preparing a microemulsion system of nano essential oil by cooling the mixture to 25° C., homogenizing the mixture by ultrasonication using an ultrasonic homogenizer over a period ranging from 30 to 60 minutes to achieve a droplet size smaller than 100 nm, controlling the quality of the resultant product by dissolution in water and measurement of the transparency, in which if the required transparency is not met, continue to heat and measure the transparency every 30 minutes until the required transparency is met, stopping the reaction, and performing emulsifying on the solution mixture in an emulsifying device at a stirring rate ranging from 400 to 800 rpm to obtain the microemulsion system of nano essential oil.

In a process according to an embodiment of the invention, in step (ii), the weight ratio of diethylene glycol monoethyl ether and lecithin is 5:1.

In a process according to another embodiment of the invention, in step (iii), the carrier is added to the dispersed phase at the weight ratio of 2:1.

In a process according to yet another embodiment of the invention, in step (iv), add the solution mixture obtained in step (iii) to Capryol 90 (propylene glycol monocaprylate) at the weight ratio of 4:1.

DETAILED DESCRIPTION OF THE PREFERRED EMBODIMENTS

Figure 1:
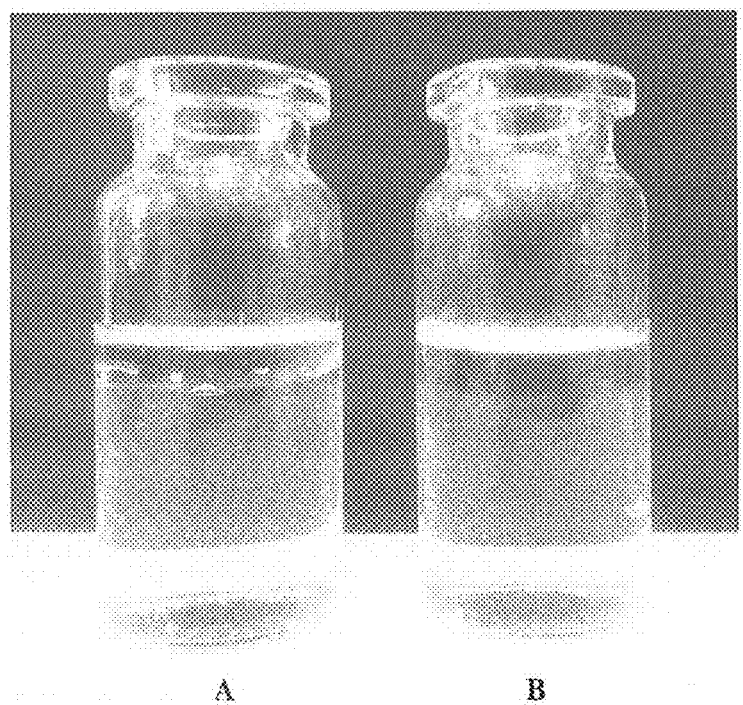
FIG. 1 is an image to compare the dispersibility in water of between (A) essential oil and (B) nano essential oil obtained by the process according to the invention.

A process for producing a microemulsion system of nano essential oil according to the invention is performed as follows:

(i) Preparing a dispersed phase by heating an essential oil to a temperature between 60 and 100° C. The heating enables the dispersed phase to be better combined with a carrier.

(ii) Preparing the carrier by heating a mixture of diethylene glycol monoethyl ether and lecithin at the weight ratio of between 5:1.5 and 6:1, preferably 5:1, to a temperature between 60 and 100° C. under vacuum by using a rotary vacuum evaporator system over a period ranging from 30 to 60 minutes, followed by cooling the mixture to 30° C., then respectively ultrasonicating for 30 minutes, magnetic stirring, and heating at a temperature between 60 and 100° C. for 30 minutes, collecting the solution and introducing into the rotary vacuum evaporator system, and continuing to stir at 100° C. over a period ranging from 30 to 60 minutes.

When used, the essential oils can be denatured by light, and temperature, and are often destroyed in the digestive tract. Therefore, there is a demand for a process for producing essential oil microdroplets of small size with capsule, having a stable structure, a non-binding property, and a high solubility. Because the microemulsion system according to the invention is used in food and pharmaceutical industries, the carriers selected for use must be highly safe, and non-toxic with few side effects. Diethylene glycol monoethyl ether is a mixture of propylene glycol monoester and fatty acid dieter composed mainly of caprylic acid. The contents of monoester and diester vary for the two types (Type I and Type II) of propylene glycol monocaprylate with acknowledged safety.

With properties as a specific soluble carrier for injections, solutions (in pharmacy and veterinary), and agents for adjustment and stabilization of viscosity, and for formation of microemulsion liquids, diethylene glycol monoethyl ether helps to emulsify and form good microemulsion systems with increased absorption. However, since the carrier if used on the skin in high dosages will cause irritation, the maximum level of essential oil-based carrier must not exceed 10%. Lecithin is a very popular food additive and is acknowledged as safe to human health by the Europe.

Lecithin is essentially a type of phospholipid which is found in every cell of the human body. The chemical formula of lecithin shows that lecithin is a fat, but a structural component of the lecithin molecule can dissolve in water. This allows lecithin to emulsify essential oils, and advocate their dispersion in water. However, lecithin itself is only capable of loading up to 5-10% of the active ingredient and for effective loading, it is required for a certain level of purity, and complicated separation processes.

In addition, the lecithin price is very high, with the cosmetic production processes using only lecithin still containing impurities, being not refined, and having low delivery efficiency. Therefore, in order to form a stable and safe microemulsion system for users that the product can be used both on the skin and orally, the combination of diethylene glycol monoethyl ether and lecithin at the weight ratio of 5:1.5 to 6:1, preferably 5:1, to form an optimal delivery efficiency for the essential oil of up to 30%, while ensuring formation of nanodroplets with a size smaller than 100 nm that are completely dispersed in water to form a homogeneous transparent solution system. This is a complete difference that has produced advantageous delivery efficiency when compared to existing processes.

If the ratio of diethylene glycol monoethyl ether and lecithin is less than 5:1.5, it is possible that the resulting carrier may not carry the whole amount of oil, resulting in the droplet sizes being inconsistent, and the resultant system being unstable and likely to have layer separation. If the above ratio is higher than 6:1, the lecithin amount will remain in the system, which goes wasted and makes the system less stable.

In the carrier preparing, the invention uses diethylene glycol monoethyl ether and lecithin with a studied ratio, that is different from the known solutions, particularly from the solution described in CN105640846 A (Wang Lu) for producing peppermint essential oil emulsion preparation. The preparation when directly applied on the skin inducing a whitening effect is in oil emulsion form, used for direct application and no applicable to other products. This process only involves the use of lecithin herein for stabilization of the system, but not for retention of the droplet stability in a long term, and the resultant emulsion system is insoluble in water, which is completely different from when using diethylene glycol monoethyl ether and lecithin at the same ratio according to the invention. According to the invention, the studied ratio by the inventors under said conditions helps to reduce the impact on the lecithin structure, and the diethylene glycol monoethyl ether helps to increase the delivery capacity of the active substance, and the combination of the two substances at said ratio allow the loading capacity to increase as many times as using lecithin alone.

(iii) Adding the carrier to the dispersed phase at the weight ratio of between 2:1.5 and 2:1, preferably 2:1, while keeping the temperature of the dispersed phase from 60 to 100° C. after addition of the carrier, while simultaneously stirring at a rate ranging from 400 to 800 rpm under vacuum over a period ranging from 30 to 60 minutes; then introducing the whole solution mixture into a high-pressure homogenizer integrated with a dispersion nozzle.

At the weight ratio of the carrier to the dispersed phase ranging from 2:1.5 to 2:1, preferably 2:1, the reaction yield is the most optimal that ensures that all substances in the dispersed phase are fully delivered by the carrier, and there is no excess carrier in the system.

The combination of the carrier as a mixture of diethylene glycol monoethyl ether and lecithin, and specialized processing steps helps to achieve the most optimal interaction with and encapsulation of the dispersed phase. The use of the high-pressure homogenizer integrated with a dispersion nozzle increases the encapsulation efficiency while improving the durability of biofilm, allowing the oleophilic heads to fully interact and form optimal bonds. The inventors have produced a dispersion nozzle for integration with the homogenizer to not only utilize high-pressure homogenization to form droplets, but also help to disperse the droplets right after their formation in avoidance of droplet aggregation before addition of other substances in the subsequent step. This plays a very important role in increasing the stability of the nano system, which helps increase the yield and stable duration of the system.

(iv) Adding the solution mixture obtained in step (iii) to Capryol 90 (propylene glycol monocaprylate) at the weight ratio of between 4:1.5 and 4.5:1, preferably 4:1 while keeping the mixture temperature between 60 and 100° C. after the addition of Capryol 90, then stirring at a rate ranging from 400 to 800 rpm under vacuum over a period ranging from 30 to 60 minutes.

From theoretical and empirical studies, the inventors found that in order to prepare a nano essential oil which dissolves well in water, the emulsion system needs to be in the form of an oil-in-water emulsion. The selection of an emulsifier to increase the stability of the microemulsion system is based on the properties of the microemulsion system (e.g., oil-in-water microemulsion, water-in-oil microemulsion, etc.). Therefore, the inventors select the emulsifier Capryol 90 (propylene glycol monocaprylate) because Capryol 90 (propylene glycol monocaprylate) is a non-ionic water-insoluble surfactant used as a surfactant in oil-based emulsion and microemulsion formulations with no toxicity and great safety. The addition of the solution mixture obtained in step (iii) to Capryol 90 (propylene glycol monocaprylate) at the weight ratio of between 4:1.5 and 4.5:1, preferably 4:1, makes sure that the HLB index of the system is suitable to make it possible for dispersion in the aqueous phase, wherein if the ratio is lower, the system will be oil-based and difficult to disperse well in water, and if the ratio is greater, the system will be water-based but less stable.

(v) Preparing a microemulsion system of nano essential oil by cooling the mixture to 25° C., homogenizing the mixture by ultrasonication using an ultrasonic homogenizer over a period ranging from 30 to 60 minutes to achieve a droplet size smaller than 100 nm, controlling the quality of the resultant product by dissolution in water and measurement of the transparency, in which if the required transparency is not met, continue heating and measure the transparency every 30 minutes until the required transparency is met, stopping the reaction, and performing emulsifying on the solution mixture in a emulsifying device at a stirring rate ranging from 400 to 800 rpm at the room temperature to obtain the microemulsion system of nano essential oil.

Nanodroplets tend to aggregate; therefore it is required to provide sufficient energy to overcome the binding forces. The use of ultrasonic homogenizer is an effective means of nanodroplet dispersion and reduction of nanodroplet size, which forms droplets with smaller and more uniform size. The dispersion and the aggreagation disruption of nanodroplets result from gas penetration by ultrasound. As the ultrasound is propagated in the solvent, alternating cycles between the high and low pressures are formed, which makes an impact on the binding forces of the nanodroplets. At the same time, when a series of bubbles burst, it forms a very high pressure on the nanodroplet beams so that they separate easily from each other. From the experiments, the inventors identify the ultrasonication timepoints to help form the droplet structure of product interest.

From theoretical and empirical studies, the inventors found that to produce nano essential oil with good solubility in water, the microemulsion system needs to be in the form of an oil-in-water emulsion. Selection of an emulsifier to increase the stability of the microemulsion system is based on the properties of the microemulsion system (e.g., oil-in-water microemulsion, water-in-oil microemulsion, etc.).

The microemulsion system obtained by a process according to the invention has a pH ranging from 7 to 7.4. With this pH value, the microdroplets are stable because in this neutral environment, the bonds between the essential oil and the carrier are retained in the dispersion process, while if the microemulsion system has a $pH<7$, the bonds are weakened, leading to destruction of the essential oil nanodroplets in the digestive tract.

The nano essential oil microemulsion system obtained by a process according to the invention has a hydrophilic-lipophilic balance (HLB) index ranging from 13 to 18, therefore it is a water-based microemulsion system. This microemulsion system has microdroplets containing water-based, and non-aggregated essential oil, wherein the size of the droplets is uniform and stable, so it can increase the solubility in water, thereby increasing its applicability to many various types of products.

EXAMPLES

Example: Production of 225 g of the Microemulsion System of Nano Essential Oil Preparation of a dispersed phase: 60 g of essential oil was stirred at 400 rpm, being heating at 60° C. until uniformity was achieved with a magnetic hotplate stirrer (IKA C-MAG HS 7; power: 1000 W).

Preparation of a carrier: A mixture of 100 g of Transcutol P diethylene glycol monoethyl ether and 20 g of lecithin was subjected to heating to 60° C. for 40 minutes by a rotary vacuum evaporator system (RV 10 Digital V-C IKA; power of 1400 W). Then, the mixture is left to cool to 30° C., respectively followed by ultrasonication by an ultrasonic atomizer nozzle for 30 minutes, magnetic stirring, and heating by magnetic hotplate stirrer (IKA C-MAG HS 7; power: 1000 W) at 60° C. for 30 minutes. The solution was collected and introduced into a rotary vacuum evaporator system (RV 10 Digital VC IKA; power: 1400 W), and continued with stirring at 100° C.

120 g of the carrier was added to 60 g of the dispersed phase prepared above. The dispersed phase with the added carrier was further heated to 60° C. and stirred at 600 rpm under vacuum for 40 minutes by using a magnetic hotplate stirrer (IKA C-MAG HS 7; power: 1000 W). Then the whole solution mixture was introduced into a high pressure homogenizer (maximum pressure: 60 Mpa) integrated with a dispersion nozzle.

Capryol 90 was added to the mixture obtained in step (iii) at the weight ratio of 1:4, corresponding to 45 g of Capryol 90 to 180 g of the mixture, while keeping the mixture temperature between 60 and 100° C. after the addition of Capryol 90. The resultant was stirred at 600 rpm under vacuum for 40 minutes by using magnetic hotplate stirrer (IKA C-MAG HS 7; power: 1000 W) to yield 225 g of mixture.

The obtained mixture was left to cool to 25° C. and homonized using an ultrasonic homogenizer (200-400 W). Since the time period of ultrasonication would make an impact on the droplet size, it is necessary to ultrasonicate from 10 to 20 minutes in order to achieve droplets size of between 100 and 500 nm; it is necessary to ultrasonicate from 30 to 60 minutes in order to achieve a droplets size smaller than 100 nm.

The quality of the resultant product was controlled by dissolving the product in water and measuring the transparency, in which if the required transparency was not met, heating was continued and the transparency was measured every 30 minutes until the required transparency was met. The reaction was stopped, and the temperature was slowly lowered to 50° C. At 50° C., emulsification was performed on the solution mixture at a rate of 500 rpm for 30 minutes.

Before filling, 225 g of the microemulsion system of nano essential oil with good water dispersibility was collected.

By a UV-vis spectroscopic method, the inventors have found that the positions of the peaks of the essential oil material and peaks of the microemulsion system of nano essential oil were completely overlapped. This shows that the microemulsion system obtained by the process according to the invention still retained its structure and essential oil activity during nanoization. The UV-Vis spectroscopic method was used to quantify the content of the essential oil in the microemulsion system. The results showed that the concentration of the essential oil in the microemulsion system of nano essential oil fell in the range of 25-30%.

Figure 2:
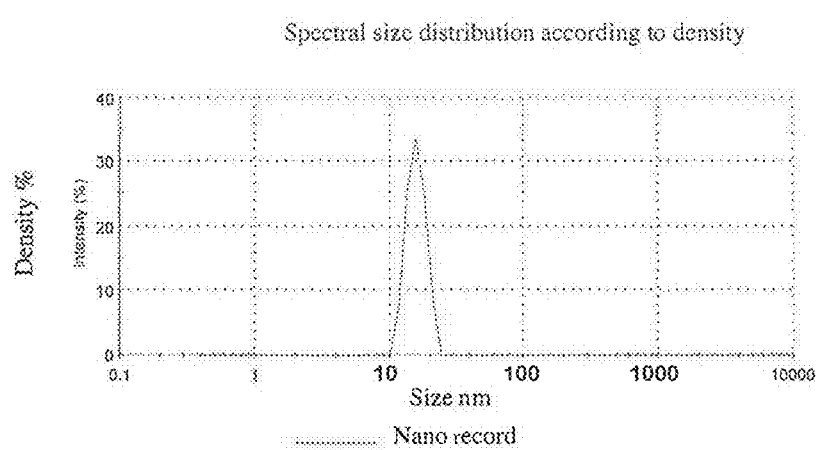
FIG. 2 represents a TEM spectrum of essential oil nanodroplets with size smaller than 100 nm obtained by the process according to the invention.

Size measurement of the essential oil nanodroplets by a scanning transmission electron microscope is shown in FIG. 2, which shows the droplet size ranging from 10 nm to 50 nm that accounts for the substantially maximum percentage of 100% in the solution.

The droplet size was measured by Dynamic Light Scattering (DLS): The suspended droplets in a liquid constantly underwent random movements, and the droplet size directly affects their velocity. Smaller droplets move faster than larger droplets. In DLS, light passes through a sample, and the scattered light is detected and recorded at a certain angle.

Zeta potential or dynamic potential: the potential between the dispersed phase and the dispersion medium.

The following table shows the measurement data by the Dynamic Light Scattering (DLS) method:

| Nano essential oil with experiments to achieve droplet sizes smaller than 100 nm | | Diameter (nm) | Density % | Width (nm) |
|---|---|---|---|---|
| Average droplet size (diameter: nm): 15.90 | Spectral peak 1 | 15.90 | 100 | 2.516 |
| Pdl: 0.136 | Spectral peak 2 | 0.00 | 0.00 | 0.00 |
| Probability: 0.939 | Spectral peak 3 | 0.00 | 0.00 | 0.00 |
| Evaluation result: good | | | | |

Analysis: data from this table reflected an average droplet size of 15.90 nm, accounting for a density of 100% in the system.

| Size (nm, according to TEM) | Size (nm, according to DLS) | Zeta potential (mV) | Stability (month) | Solubility in water |
|---|---|---|---|---|
| 10-50 | 10-50 | −40 | >12 | good solubility in water, after dissolution in water, the system is stable for >7 days |

Above results show that, by using of diethylene glycol monoethyl ether and lecithin in combination with Capryol 90, it is possible to obtain a microemulsion system containing microdroplets of small size, ranging from 10 nm to 50 nm, and high stability (>12 months), and good solubility in water, and after being dissolved in water the system is stable for >7 days. Large of value Zeta potential indicates that the droplets are highly charged and that the system tends to be stable.

According to FIG. 1, which is a picture comparing the dispersibility in water between a known essential oil and the nano essential oil obtained by the process according to the invention, vial A contained the known essential oil dispersed in water, and vial B contained the nano essential oil obtained by the process according to the invention; both of the essential oils were dispersed in water. The nano essential oil obtained by the process according to the invention was completely dispersed in water to form a transparent and homogeneous solution, while the known essential oil was insoluble in water and floated on the surface.

According to FIG. 2, which represents a TEM spectrum of essential oil nanodroplets obtained by the process according to the invention, it is shown that the average droplet size fell in the range of 10-50 nm.

ADVANTAGEOUS EFFECTS OF THE INVENTION

The process for producing a microemulsion system of nano essential oil according to the invention has been successful in the production of the microemulsion system that contains essential oil microdroplets with a size ranging from 10 to 50 nm, and of great uniformity and good solubility in water while retaining the structure and activity of an essential oil during nanoization.

The substances used in the process for producing nano essential oil with good water dispersibility are highly safe, non-toxic and have few side effects; therefore the microemulsion system of nano essential oil obtained by the process according to the invention is highly safe when used.

The process according to the invention is simple, easy to implement, and suitable for the current practice in Vietnam.

We claim:

1. A process for producing a microemulsion system of nano essential oil comprising the steps of:
   (i) preparing a dispersed phase by heating an essential oil to a temperature between 60 and 100° C., the essential oil selected from a group consisting of: Basil; Rose; Amber; Bergamot; Rosemary; Black tea; Black pepper; Tea tree; Tabac; Cedarwood; Thyme; Fig leaf; Clove; Ylang Ylang; Ambroxan; Frankincense; Grapefruit; Daisy; Geranium; Vetiver; Saffron; Lavender; Sandalwood; Oud; Nutmeg; Musk; Whisky wine; Palmarosa; Jasmine; Rum; Patchouli; Magnolia flower; and Cinnamon;
   (ii) preparing a carrier by heating a mixture of diethylene glycol monoethyl ether and lecithin at a weight ratio of between 5:1.5 and 6:1 to a temperature ranging from 60° C. to 100° C. under vacuum by using a rotary vacuum evaporator system, followed by cooling the mixture to 30° C., then ultrasonicating the mixture for 30 minutes, followed by magnetic stirring, and then heating the mixture at a temperature from 60° C. to 100° C., within 30 minutes, collecting the mixture and introducing into the rotary vacuum evaporator system, and continuing to stir at 100° C.;
   (iii) adding the carrier to the dispersed phase obtained in step (i) at a weight ratio of between 2:1.5 and 2:1 while keeping a dispersed phase temperature between 60° C. and 100° C. after addition the carrier, while simultaneously stirring at a rate ranging from 400 to 800 rpm under vacuum; then passing the mixture through a system of a high-pressure homogeneous machine integrated with a dispersion nozzle;
   (iv) adding the mixture obtained in step (iii) to Capryol 90 (propylene glycol monocaprylate) at a weight ratio of between 4:1.5 and 4.5:1 while keeping the mixture temperature between 60° C. and 100° C. after the addition of Capryol 90, then stirring at a rate ranging from 400 to 800 rpm under vacuum; and
   (v) preparing a microemulsion system of nano essential oil by cooling the mixture obtained in step (iv) to 25° C., homogenizing the mixture by ultrasonication using an ultrasonic homogenizer over a period from 30 to 60 minutes to achieve a droplet size smaller than 100 nm, controlling a quality of a resultant product by dissolution in water and performing emulsifying on the mixture in an emulsifying device at a stirring rate ranging from 400 to 800 rpm to obtain a microemulsion system of nano essential oil.

2. The process according to claim 1, in which in step (ii), the weight ratio of diethylene glycol monoethyl ether and lecithin is 5:1.

3. The process according to claim 1, in which in step (iii), the weight ratio of the carrier and the dispersed phase is 2:1.

4. The process according to claim 1, in which in step (iv), the weight ratio of the solution mixture obtained in step (iii) and Capryol 90 (propylene glycol monocaprylate) is 4:1.

* * * * *